United States Patent [19]

Herrmann et al.

[11] Patent Number: 5,312,951
[45] Date of Patent: May 17, 1994

[54] 3,4-DIMETHYL-2,5,6-TRIS(P-SULFONATOPHENYL)-1-PHOSPHANORBORNADIENE, PROCESS FOR THE PREPARATION THEREOF AND PROCESS FOR THE HYDROFORMYLATION OF OLEFINNICALLY UNSATURATED COMPOUNDS

[75] Inventors: Wolfgang A. Herrmann, Giggenhausen; Rainer Manetsberger, Munchen; Christian Kohlpaintner, Stephanskirchen; Helmut Bahrmann, Hamminkeln, all of Fed. Rep. of Germany

[73] Assignee: Hoechst Aktiengesellschaft, Fed. Rep. of Germany

[21] Appl. No.: 78,975

[22] Filed: Jun. 17, 1993

[30] Foreign Application Priority Data

Jun. 20, 1992 [DE] Fed. Rep. of Germany ....... 4220267

[51] Int. Cl.$^5$ ................................................ C07F 9/02
[52] U.S. Cl. ...................................... 558/45; 568/454
[58] Field of Search ............... 558/45; 568/454, 45, 568/451

[56] References Cited

U.S. PATENT DOCUMENTS

| | | | |
|---|---|---|---|
| 3,166,581 | 6/1965 | Vegter | 558/45 |
| 4,287,189 | 9/1981 | Hurt | 558/45 |

FOREIGN PATENT DOCUMENTS

| | | | |
|---|---|---|---|
| 2726807 | 12/1977 | Fed. Rep. of Germany | 558/45 |
| 284986 | 10/1970 | U.S.S.R. | 558/45 |
| 3406640 | 6/1972 | U.S.S.R. | 558/45 |

*Primary Examiner*—Werren B. Lone
*Attorney, Agent, or Firm*—Jordan B. Bierman

[57] ABSTRACT

The chemical compound 3,4-dimethyl-2,5,6-tris(p-sulfonatophenyl)-1-phosphanorbernadiene, a process for the preparation thereof and a process for the hydroformylation of olefinically unsaturated compounds with the use of catalysts which contain the aforementioned chemical compound.

6 Claims, No Drawings

3,4-DIMETHYL-2,5,6-TRIS(P-SULFONATO-PHENYL)-1-PHOSPHANORBORNADIENE, PROCESS FOR THE PREPARATION THEREOF AND PROCESS FOR THE HYDROFORMYLATION OF OLEFINNICALLY UNSATURATED COMPOUNDS

The invention relates to the chemical compound 3,4-dimethyl-2,5,6-tris(p-sulfonatophenyl)-1-phosphanorbornadiene, a process for the preparation thereof, and the hydroformylation of olefinically unsaturated compounds with the use of catalysts which contain said compounds.

BACKGROUND OF THE INVENTION

Complex compounds which contain, as a central atom, a metal of Group VIII of the Periodic Table of the Elements (IUPAC version) and, as ligands, P(III) compounds, phosphines, or phosphites, as well as possibly other groups capable of complex formation, have recently been gaining increased importance as catalysts. The reaction, performed industrially on a large scale, of olefins with synthesis gas to give aldehydes (hydroformylation) is carried out in the presence of catalyst systems which are composed of cobalt and, in particular, rhodium and triphenylphosphine. Catalysts based on phosphine-containing complex compounds have also proven themselves useful for the reaction of methanol with synthesis gas to give higher alcohols, in particular ethanol and propanol (homologization). The ligands are primarily present in excess in the cases mentioned, so that the catalyst system is composed of a complex compound and free ligand. In accordance with the solubility of the catalysts in organic media, the reactions are carried out in a homogeneous phase.

The reaction can also be carried out in a heterogeneous reaction system; an advantage of this process variant is the simple and mild separation of the catalyst, which is present in aqueous solution, from the water-insoluble reaction product. This principle is employed by, for example, the process described in DE-C2 27 00 904 for the addition of hydrogen cyanide to an unsaturated organic compound having at least one ethylenic double bond. For the preparation of aldehydes by reaction of olefins with carbon monoxide and hydrogen, according to the process of DE-C2 26 27 354, rhodium in metallic form, or in the form of compounds thereof, is used together with a water-soluble phosphine, e.g. the alkali metal salt of triphenylphosphine-trisulfonic acid ("TPPTS") as a catalyst.

The known two-phase processes have proven themselves very effective on an industrial scale. Nevertheless, efforts are being expended to improve the process even further. Thus, attempts are being made to increase and prolong the activity of the catalysts by modifying the complex ligands to reduce further the specific catalyst requirements—both rhodium and ligand—and hence the production costs. Economic grounds are also decisive for working towards a marked reduction of the phosphine/rhodium ratio. Furthermore, attempts are being made to develop specially adapted ligand systems which solve individual problems. As an example, the additional improvement in selectivity with respect to the formation of unbranched aldehydes can be mentioned. However, the opposite aim, the construction of branched-chain products, can also be of interest with respect to enantioselective syntheses. In this regard, it should be noted that several million tons of hydroformylation products are prepared annually, so that even a small change in selectivity in one direction or the other has economically significant consequences.

SUMMARY OF THE INVENTION

The invention comprises the chemical compound 3,4-dimethyl-2,5,6-tris(p-sulfonatophenyl)-1-phosphanorbornadiene (hereinafter NORBOS).

The invention further relates to a process for the preparation of NORBOS which comprises reacting 3,4-dimethyl-2,5,6-triphenyl-1-phosphanorbornadiene with a solution of sulfur trioxide in sulfuric acid at temperatures of 0° to 20° C.; gradually bringing the resulting mixture to room temperature with stirring; and stirring the mixture for a further 20 to 30 minutes while maintaining the temperature at 0° to 50° C., in particular 0° to 20° C.; diluting the reaction mixture with water, or adding it to ice, and then working up the mixture.

The invention is also directed to a process for the preparation of aldehydes by reaction of monoolefins, unconjugated polyolefins, cycloolefins, or derivatives of these compound classes, with carbon monoxide and hydrogen at temperatures of 20° to 150° C. and pressures of 0.1 to 30 MPa in the presence of rhodium compounds dissolved in water and containing complex phosphines as catalysts. It comprises using NORBOS as the phosphine.

Surprisingly, it has been found that the novel phosphorus compound is outstandingly suitable as a component of water-soluble catalyst systems, in particular those which are used for carbonylation reactions. NORBOS is distinguished by high resistance to oxidation and particular stability of the carbon-phosphorus bonds. In a complex with rhodium, a preferred hydroformylation catalyst results which permits the reaction of olefinically unsaturated compounds to give aldehydes with high activity A $$A = \frac{\text{mol aldehyde}}{\text{mol Rh} \cdot \text{minute}}$$

and productivity P $$P = \frac{\text{g of aldehyde}}{\text{ml of catalyst solution} \cdot \text{hour}}$$

DETAILED DESCRIPTION OF THE INVENTION

The starting compound 3,4-dimethyl-2,5,6-triphenyl-1-phosphanorbornadiene required for the preparation of NORBOS can be obtained according to the prior art in good yield in a two-stage synthesis. In the first process step, phenyldichlorophosphine or phenyldibromophosphine, or a mixture thereof, is reacted with dimethylbutadiene to give the 1-halo-2,5-dihydrophospholium salt, which is dehydrohalogenated by 2-methylpyridine to give 3,4-dimethyl-1-phenylphosphole. The reaction of the phosphole with diphenylacetylene in the second process step produce 3,4-dimethyl-2,5,6-triphenyl-1-phosphanorbornadiene.

The phosphanorbornadiene can be sulfonated without preliminary purification. The sulfonation agent used according to the invention is oleum, i.e. a solution of $SO_3$ in sulfuric acid. The $SO_3$ concentration in this solution is expediently 20% to 65% by weight, based on the solution. In order to carry out the reaction under mild conditions, the phosphorus compound is added to the SO₃ reagent in portions; the temperature is maintained at 0° to 20°, preferably 0° to 5° C., the mixture is gradually brought to room temperature with stirring, and is allowed to react further in the same temperature range for 20 to 30 minutes. The reaction mixture is then, preferably at 0° to 50° C., especially 0° to 20° C., diluted using water or, better, ice and then neutralized, preferably with alkali metal carbonate or alkali metal hydroxide. The solution is concentrated, filtered off from the precipitated alkali metal sulfate, and the filtrate is placed in methanol. If necessary, the purification operation, concentration, filtration, and placing in methanol can be repeated. Finally, the sulfonated compound is obtained by evaporating the methanol solution to dryness. The crude product can be used directly as a component of catalyst systems. The novel compound is obtained in pure form from the crude product by, for example gel permeation chromatography, as required for physicochemical characterization.

Trisodium NORBOS is a yellowish-white powder which dissolves very readily in water. From the sodium salt, as well as from other alkali metal salts, the free acid, as well as the salts of other metals, can be prepared, for example, by ion exchange.

NORBOS forms complexes with various metals, among which those with rhodium have particular importance as catalysts for the hydroformylation of olefinically unsaturated compounds. Rhodium and phosphorus compounds (in the form of the trisodium or other water-soluble salts of NORBOS) are advantageously not used in a stoichiometric ratio; it is more advantageous to employ NORBOS in excess. The ratio of rhodium to NORBOS can then be varied within wide ranges; per mole of rhodium, about 1 to 15 mol of NORBOS can be used. Preference is given to a ratio of 1 mol of rhodium to 3 to 15 and, in particular, 8 to 13 mol of NORBOS.

Rhodium can be used as the metal or as a compound. When in the metallic state, it is either in the form of finely divided particles or precipitated in a thin coating on a support such as activated charcoal, calcium carbonate, aluminum silicate, or clay. Rhodium compounds which are useful are those substances which are water soluble, or become water soluble, under the reaction conditions. The various rhodium oxides, salts of inorganic hydracids and oxyacids, and salts of aliphatic monocarboxylic acids and polycarboxylic acids are suitable. Examples of rhodium salts are rhodium nitrate, rhodium sulfate, rhodium acetate, rhodium 2-ethylhexanoate, and rhodium malonate. Rhodium-halogen compounds, however, because of the corrosive behavior of the halide ions, are less useful. Furthermore, rhodium carbonyl compounds such as $Rh_3(CO)_{12}$, $Rh_6(CO)_{16}$, or complex salts of rhodium, e.g. cyclooctadienylrhodium compounds, can be used. Preference is given to rhodium oxide and, in particular, rhodium acetate and rhodium 2-ethylhexanoate. It is assumed that, in the presence of water gas under the conditions of the hydroformylation reaction, water-soluble rhodium complexes are formed which contain carbon monoxide and NORBOS as ligands. They, together with the excess NORBOS dissolved in the water, constitute the catalyst system.

The catalyst solution is prepared from the components either in the hydroformylation reactor, or previously in a separate apparatus, and then introduced into the reactor. The weight concentration of rhodium in the aqueous catalyst solution is 20 to 1000 ppm (based on the solution), preferably 100 to 600 ppm and, in particular, 200 to 400 ppm.

The reaction of the olefin with carbon monoxide and hydrogen is carried out at pressures of about 0.1 to about 30 MPa, preferably to 1 to 12 MPa and, in particular, 3 to 7 MPa. The composition of the synthesis gas, i.e. the volume ratio of carbon monoxide to hydrogen can extend over wide ranges and, for example, can vary between 1:10 to 10:1. Gas mixtures are generally used in which the volume ratio of carbon monoxide and hydrogen is about 1:1 or varies only slightly from this value in one direction or the other.

The reaction temperature is from about 20° to 150° C., preferably 80° to 140° C. and, in particular, 100° to 125° C.

The reaction of the reactants present in the liquid and gaseous phases is carried out in conventional reactors. The course of the reaction is decisively influenced by the fact that the aqueous catalyst solution must be saturated with the liquid or gaseous hydrophobic olefin and the synthesis gas. Therefore it is necessary to produce as large a contact surface as possible between the phases. It has proven to be successful to agitate the liquid reactor contents—catalyst solution, possibly liquid olefin, and reaction product—intensively and to feed the gaseous reactants synthesis gas and possibly olefin—to the liquid phase via distribution devices. It has further proven to be highly successful to keep the proportion of the organic phase in the reaction mixture low. Surprisingly, the organic phase does not contribute to the solubility of the reactants in the aqueous phase and the reaction product is prevented from entering into undesired side reactions which cannot be prevented when the residence time of the product in the reactor is increased. Accordingly, a volume ratio of aqueous to organic phase of 1:1 to 100:1, and preferably 10:1 to 100:1 is desirable. For this purpose, an appropriate part of the reaction mixture can be continuously removed from the reactor, the aqueous and organic phases separated from each other, and the aqueous phase returned to the reactor. The reaction can be carried out batchwise or, preferably, continuously.

The process according to the invention can be successfully applied to the reaction of monoolefins, unconjugated polyolefins, cycloolefins, and derivatives of these unsaturated compounds. The olefins can be straight-chain or branched, the double bonds can be terminal or internal. Examples of olefins which can be used in the novel process are ethylene, propylene, butene-1, butene-2, pentene-1, 2-methylbutene-1, hexene-1, hexene-2, heptene-1, octene-1, octene-3, 3-ethylhexene-1, decene-1, undecene-3, 4,4-dimethylnonene-1, dicyclopentadiene, vinylcyclohexene, cyclooctadiene, and styrene. Derivatives of the olefin types mentioned which can be hydroformylated by the claimed procedure are, for example, alcohols, aldehydes, carboxylic acids, esters, nitriles, and halogens. Preferred are allyl alcohol, acrolein, methacrolein, crotonaldehyde, methyl acrylate, ethyl crotonate, diethyl fumarate, diethyl maleate, and acrylonitrile. The process is used with particular success for the hydroformylation of olefins and olefin derivatives having 2 to 12 carbon atoms.

The following examples illustrate the invention without restricting it to these embodiments.

1. Preparation of NORBOS

(a) 3,4-Dimethyl-1-phenylphosphole (according to A. Breque et al., Synth., 1981, 12, 984)

In a 1000 ml flask equipped with a stirrer, 44.7 g (250 mmol) of phenyl dibromophosphine is mixed with 66.9 g (250 mmol) of phenyldichlorophosphine for 30 minutes at room temperature under nitrogen. 42.0 g (511 mmol) of dimethylbutadiene is then added to the homogeneous solution while cooling with ice, and the resulting mixture is stirred with further cooling for 24 hours. The resulting suspension is allowed to stand for a further 10 days at room temperature, and is completely transformed during this time into a white, crystalline mass; the solid is then broken into pieces as small as possible in the flask and covered with 300 ml of hexane and 200 ml of dichloromethane.

By blowing in nitrogen over a period of 30 minutes, the suspension is freed from excess dimethylbutadiene. A solution of 103 g (1094 mmol) of 2-methylpyridine in 100 ml of dichloromethane is added dropwise at room temperature with vigorous stirring. In the course of 24 hours, a mixture results which can be separated into two liquid phases. Following hydrolysis using 100 ml of 3N hydrochloric acid, the organic phase is separated off and is washed three times using 100 ml of water to achieve neutrality. The mixture is dried over sodium sulfate, filtered, and evaporated. The remaining liquid is extracted using 300 ml of hexane, and the extract is filtered and evaporated. The product thus obtained requires no further purification.

Yield: 71.17 g (378 mmol), (74.15% of theoretical).
$^{31}$P-NMR (161.8 MHz, $CD_2Cl_2$):= −1.3 ppm (s).

(b) 3,4-dimethyl-2,5,6-triphenyl-1-phosphanorbornadiene (according to F. Mathey et al., J. Chem. Soc. 1981, 103, 4595)

A solution of 27.94 g (158 mmol) of diphenylacetylene and 29.50 g (158 mmol) of 3,4-dimethyl-1-phenylphosphole in 100 ml of toluene are refluxed for 3 days. The reaction mixture is then evaporated to dryness under vacuum generated by an oil pump, and the residue is washed three times, each time using 70 ml of pentane. The product can be recrystallized from methylene chloride.

Yield: 44.94 g (123 mmol), (77.6% of theoretical)
$^{31}$P-NMR (161.8 MHz, $CD_2Cl_2$):= −7.4 ppm (s).

(c) Trisodium NORBOS 10.7 g (29.19 mmol) of 3,4-dimethyl-2,5,6-triphenyl-1-phosphanorbornadiene is added with ice cooling in the course of 10 minutes in small portions with intensive agitation to 60 ml of oleum (25% $SO_3$). After a reaction time of 1 hour, the batch is carefully poured over ice. The mixture is then neutralized using 25% sodium hydroxide solution and evaporated to about a fifth of the original volume. The sodium sulfate which precipitates is filtered off and the filtrate is stirred into 400 ml of methanol. Any additional sodium sulfate which precipitates is once again filtered off. The filtrate is concentrated to a few ml and injected into four times its volume of methanol. Suspended solid particles are filtered off and the filtrate is evaporated to dryness. The crude product can be used directly as a catalyst component. For physicochemical characterization, purification with the aid of gel permeation chromatography is essential.

Yield: 17.2 g (23.67 mmol), (81.8% of theoretical)

Elemental analysis calculated for $C_{26}H_{26}Na_3O_{12}PS_3$ (M=726.62): calculated: C: 42.98, H: 3.61, O: 26.42, P: 4.26, S: 13.24, found: C: 43.31, H: 3.67, O: 26.56, p: 4.45, S: 13.08.

$^{31}$P-NMR (161.8 MHz, $D_2O$):=5.3 ppm (s).
$^{31}$P-{$^1$H}-NMR (161.8 MHz, $D_2O$): −4.9 (s).
$^1$H-$^1$H-COSY-NMR-(400 MHz, $D_2O$): 2.0 (ABX, $^1$H,$^2J_{AB}$=10.2 Hz, $^2J_{AP}$=9.8 Hz, $CH_A$-P), 1.84 (ABX, $^1$H, $^2J_{AB}$=10.2 Hz, $^2J_{BP}$=10.3 Hz, $\overline{CH_B}$-P), 1.04 (s, 3H, Me), 1,78 (s, 3H, Me), 7.75 (d, 2H, $^2J_{HH}$=8.1 Hz, $C_{17,19}$-H), 7.76 (d, 2H, $^2J_{HH}$=7.9 Hz, $C_{9,11}$-H), 7.51 (d,2H, $\overline{^2J_{HH}}$=7.9 Hz, $C_{23,25}$-H), 6.94 (d, 2H, $\overline{^2J_{HH}}$=8.1 Hz, $C_{16,20}$-H), 7.10 (d, 2H,$\overline{^2J_{HH}}$=7.95 Hz, $C_{22,26}\underline{H}$) 7.24 (d, 2H,$\overline{^2J_{HH}}$=7.9 Hz, $C_{8,12}\underline{H}$).

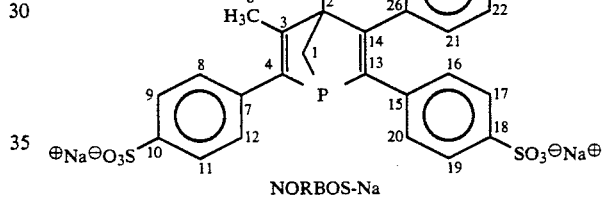

NORBOS-Na

2. Hydroformylation of propene in the presence of Rh/NORBOS as catalyst

A propylene and $CO/H_2$ mixture, composed of equal parts by volume, is fed to a stirrer-equipped 0.2 liter stainless steel autoclave at a rate such that 10 liters (S.T.P.) of exhaust gas can be withdrawn from the reactor per hour. At the same time, 325 ml of aqueous catalyst solution is circulated through the reactor per hour. The catalyst is composed of 45 mg (0.44 mmol) of rhodium (as acetate) and 5.89 mmol of P(III) compound (in the form of trisodium 10 NORBOS) which have been dissolved in degassed and nitrogensaturated water to provide 325 ml of solution. The molar ratio of phosphorus to rhodium is 13.4:1. The reaction is carried out at a temperature of 122° C. and a pressure of 5 MPa.

In the Table that follows, the results of hydroformylation of propene are compiled for different olefin inputs.

TABLE

| | | | | Hydroformylation of propene | | | | | | |
|---|---|---|---|---|---|---|---|---|---|---|
| Experiment | Propene [g/h] | Product [g/h] | Aldehyde [%] | Selectivity [n/(n + iso) %] | Tot. alcohol [%] | C3 hydrocarbon [%] | Others [%] | Activity [n + iso] | Productivity [n + iso] | Yield [n + iso %] |
| 1 | 35.70 | 29.10 | 92.80 | 78.27 | 0.35 | 4.45 | 2.40 | 61.51 | 0.19 | 44.14 |
| 2 | 37.00 | 22.50 | 90.38 | 79.76 | 0.43 | 4.47 | 4.72 | 46.32 | 0.14 | 32.07 |
| 3 | 38.00 | 56.70 | 91.13 | 78.88 | 0.52 | 4.23 | 4.12 | 117.69 | 0.37 | 79.35 |
| 4 | 44.40 | 24.80 | 91.02 | 81.39 | 0.36 | 4.49 | 4.13 | 51.41 | 0.16 | 29.67 |
| 5 | 46.90 | 42.60 | 92.67 | 78.06 | 0.37 | 4.26 | 2.70 | 89.92 | 0.28 | 49.12 |

TABLE-continued

| | | | | Hydroformylation of propene | | | | | | |
|---|---|---|---|---|---|---|---|---|---|---|
| Experiment | Propene [g/h] | Product [g/h] | Aldehyde [%] | Selectivity [n/(n + iso) %] | Tot. alcohol [%] | C3 hydrocarbon [%] | Others [%] | Activity [n + iso] | Productivity [n + iso] | Yield [n + iso %] |
| 6 | 57.60 | 47.40 | 91.73 | 78.89 | 0.34 | 5.69 | 2.24 | 99.03 | 0.31 | 44.05 |

While only a limited number of specific embodiments of the present invention have been expressly disclosed, it is, nonetheless, to be broadly construed and not to be limited except by the character of the claims appended hereto.

We claim:

1. The compound 3,4-dimethyl-2,5,6-tris(p-sulfonatophenyl)-1-phosphanorbornadiene.

2. A process for the preparation of the compound of claim 1 which comprises reacting 3,4-dimethyl-2,5,6-triphenyl-1-phosphanorbornadiene with a solution of sulfur trioxide in sulfuric acid at a sulfonation temperature of 0° to 20° C. to form a sulfonated mixture, gradually bringing said sulfonated mixture to room temperature with stirring, maintaining said sulfonated mixture at said room temperature for 20 to 30 minutes, keeping said sulfonated mixture at a holding temperature of 0° to 50° C. to form a reaction mixture, and diluting said reaction mixture with water, or adding of said reaction mixture to ice.

3. The process of claim 2 wherein, after said diluting or adding, said compound is separated from said reaction mixture.

4. The process of claim 1 wherein said holding temperature is 0° to 20° C.

5. The process of claim 2 wherein there is 20% to 65% sulfur trioxide by weight based on said solution.

6. The process of claim 2 comprising neutralizing said sulfonated mixture with an aqueous alkali metal carbonate or an alkali metal hydroxide to form a neutralized solution, concentrating said neutralized solution to form a concentrated solution, whereby alkali metal sulfate precipitates, filtering out said alkali metal sulfate to form a filtrate, introducing said filtrate into methanol to form a methanol solution, and evaporating said methanol solution to dryness.

* * * * *

UNITED STATES PATENT AND TRADEMARK OFFICE
CERTIFICATE OF CORRECTION

PATENT NO. : 5,312,951

DATED : May 17, 1994

INVENTOR(S) : Wolfgang A. Herrmann, Rainer Manetsberger, Christian Kohlpaintner and Dr. Helmut Bahrmann It is certified that error appears in the above-indentified patent and that said Letters Patent is hereby corrected as shown below:

Column 8, line 13, claim 4, change "1" to --2--.

Signed and Sealed this

Fourth Day of October, 1994

Attest:

BRUCE LEHMAN

Attesting Officer     Commissioner of Patents and Trademarks